US008283639B2

(12) United States Patent
Lane et al.

(10) Patent No.: US 8,283,639 B2
(45) Date of Patent: Oct. 9, 2012

(54) SELF-STERILIZING INPUT DEVICE

(75) Inventors: David M. Lane, Sammamish, WA (US); Abid Saifee, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 280 days.

(21) Appl. No.: 12/487,275

(22) Filed: Jun. 18, 2009

(65) Prior Publication Data
US 2009/0257912 A1 Oct. 15, 2009

Related U.S. Application Data

(63) Continuation of application No. 11/426,519, filed on Jun. 26, 2006, now Pat. No. 7,692,159.

(51) Int. Cl.
G01N 23/00 (2006.01)

(52) U.S. Cl. .......... 250/455.11; 250/453.11; 250/504 R; 250/493.1

(58) Field of Classification Search .................. None
See application file for complete search history.

(56) References Cited

U.S. PATENT DOCUMENTS

| | | | |
|---|---|---|---|
| 5,547,635 A | 8/1996 | Duthie | |
| 6,039,928 A | 3/2000 | Roberts | |
| 6,192,948 B1* | 2/2001 | Claessens et al. | 141/383 |
| 6,278,122 B1* | 8/2001 | Gagnon | 250/455.11 |
| 6,458,331 B1 | 10/2002 | Roberts | |
| 6,490,351 B1 | 12/2002 | Roberts | |
| 6,720,950 B2 | 4/2004 | Cheng | |
| 6,877,248 B1* | 4/2005 | Cross et al. | 34/275 |
| 6,903,924 B1* | 6/2005 | Tyner | 361/679.08 |
| 2003/0155531 A1* | 8/2003 | Clark et al. | 250/492.1 |
| 2004/0022668 A1* | 2/2004 | Kitchen | 422/22 |
| 2004/0028553 A1 | 2/2004 | Panico | |
| 2004/0118427 A1* | 6/2004 | Palfy et al. | 134/1 |
| 2004/0127355 A1* | 7/2004 | Manu | 502/400 |
| 2004/0265193 A1* | 12/2004 | Panice et al. | 422/186.04 |
| 2005/0028744 A1* | 2/2005 | Gantt | 119/163 |
| 2005/0052410 A1 | 3/2005 | Chen | |
| 2005/0069465 A1* | 3/2005 | McEllen | 422/121 |
| 2005/0212239 A1* | 9/2005 | Carter | 280/47.35 |
| 2005/0269254 A1* | 12/2005 | Roitman | 210/252 |
| 2006/0217789 A1* | 9/2006 | Perez | 607/94 |
| 2007/0113421 A1* | 5/2007 | Uhara et al. | 34/275 |
| 2007/0222554 A1* | 9/2007 | Hart | 340/5.6 |
| 2007/0274879 A1* | 11/2007 | Millikin | 422/186.3 |
| 2008/0065264 A1* | 3/2008 | Omura et al. | 700/231 |
| 2008/0067418 A1 | 3/2008 | Ross | |
| 2009/0317798 A1* | 12/2009 | Heid et al. | 435/6 |

FOREIGN PATENT DOCUMENTS

| | | | |
|---|---|---|---|
| DE | 3221392 A1 | * | 12/1983 |
| JP | 04061694 A | * | 2/1992 |
| JP | 06154300 A | * | 6/1994 |
| JP | 11076173 A | * | 3/1999 |
| JP | 2005211649 A | * | 8/2005 |
| JP | 2007003020 A | * | 1/2007 |

* cited by examiner

*Primary Examiner* — David A Vanore
*Assistant Examiner* — Andrew Smyth
(74) *Attorney, Agent, or Firm* — Merchant & Gould

(57) ABSTRACT

A system and method for sterilizing a surface on an input device is disclosed. A chamber is configured to enclose an input device such as a keyboard and is configured to be switched between an open and a closed state. A drive unit may be provided to switch the chamber between states. In an embodiment, the drive unit may include a motor. A sensor provides a signal to a controller when the chamber is the closed state and the controller actuates a UV light. In an embodiment, the controller actuates the drive unit and the UV light in response to a trigger. In an embodiment, the trigger may be provided from a change in state in a computer coupled to the input device.

19 Claims, 11 Drawing Sheets

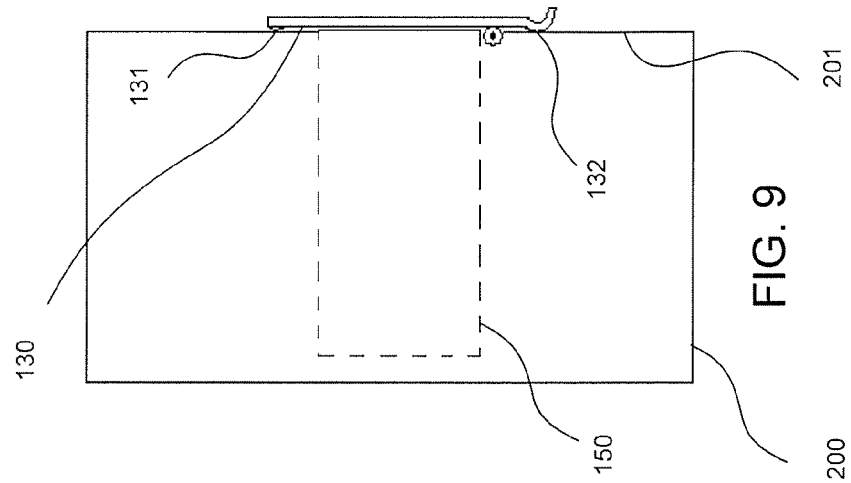
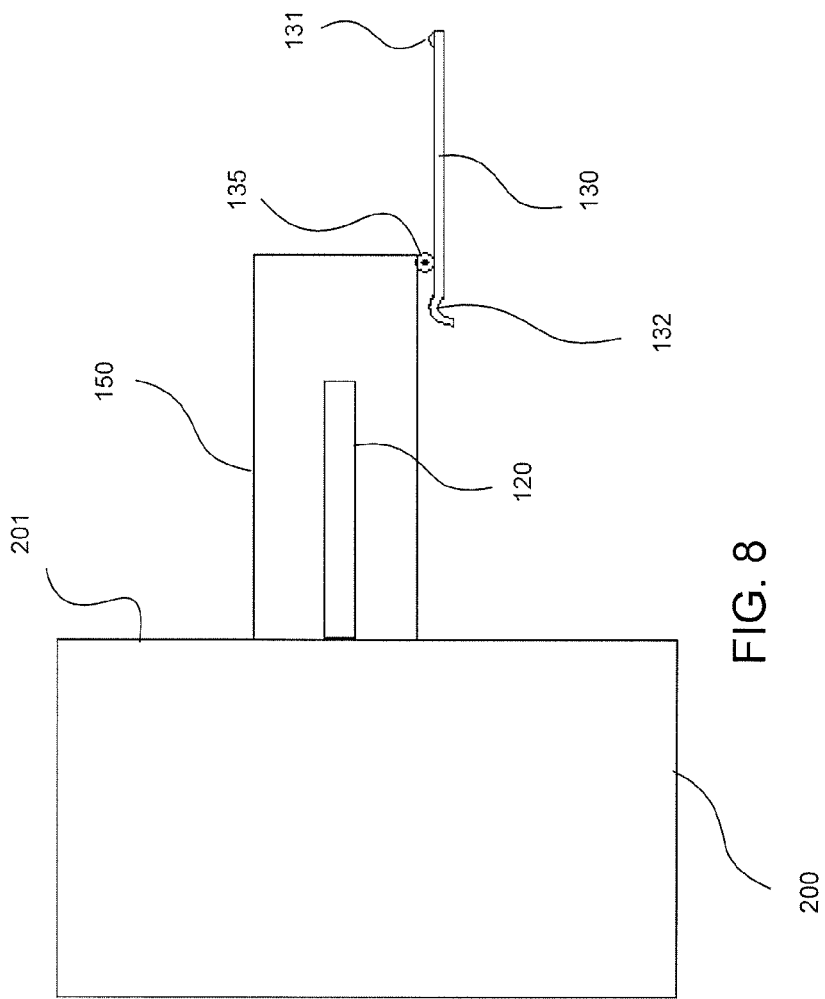

SELF-STERILIZING INPUT DEVICE

BACKGROUND

Computers have revolutionized how we process information. Individuals regularly enter and manipulate data on computer system and the computer has provided a substantial increase in productively. Typically, most computer input is handled by a user touching some input device such as a mouse or keypad or touch screen in order to input or manipulate data.

While this is effective with respect to working with the data, potential issues exist with the use of touch-based input devices. Computer input devices are often touched by many people and therefore can allow the spread of bacteria and germs from one user to the next user. While this situation is problematic in normal office settings, in health care settings the situation can become more severe. A caregiver may treat a first patient and then enter comments into a computer system via an input device. If a second caregiver also uses the same input device and then treats a second patient, there is a possibility that any bacteria or virus left on the keyboard by the first caregiver will be passed onto the second caregiver and make its way to the second patient. As can be appreciated, this can be life threatening when dealing with highly infectious diseases, especially if the disease poses a serious health concern to the second patient.

While input devices can be sterilized by being wiped with a cloth containing a disinfectant therein, this approach has drawbacks. Therefore, improvements to how input devices are sterilized would be useful.

SUMMARY

A system for sterilizing an input device is illustrated. A chamber is provided for sterilizing the input device and includes a UV light. The chamber may be switch between an open and a closed state by a drive unit. A sensor is provided to detect when the chamber is in the closed state. A controller is coupled to the sensor and may be configured to cause the drive unit to switch the chamber between positions in response to a trigger and may be configured to actuate the UV light in response to a signal received from the sensor.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Aspects of the invention are illustrated by way of example and not limited in the accompanying figures in which like reference numerals indicate similar elements and in which:

FIGS. 8 and 9 are schematic views of an alternative embodiment of a door positioner.

DETAILED DESCRIPTION

Figure 1:
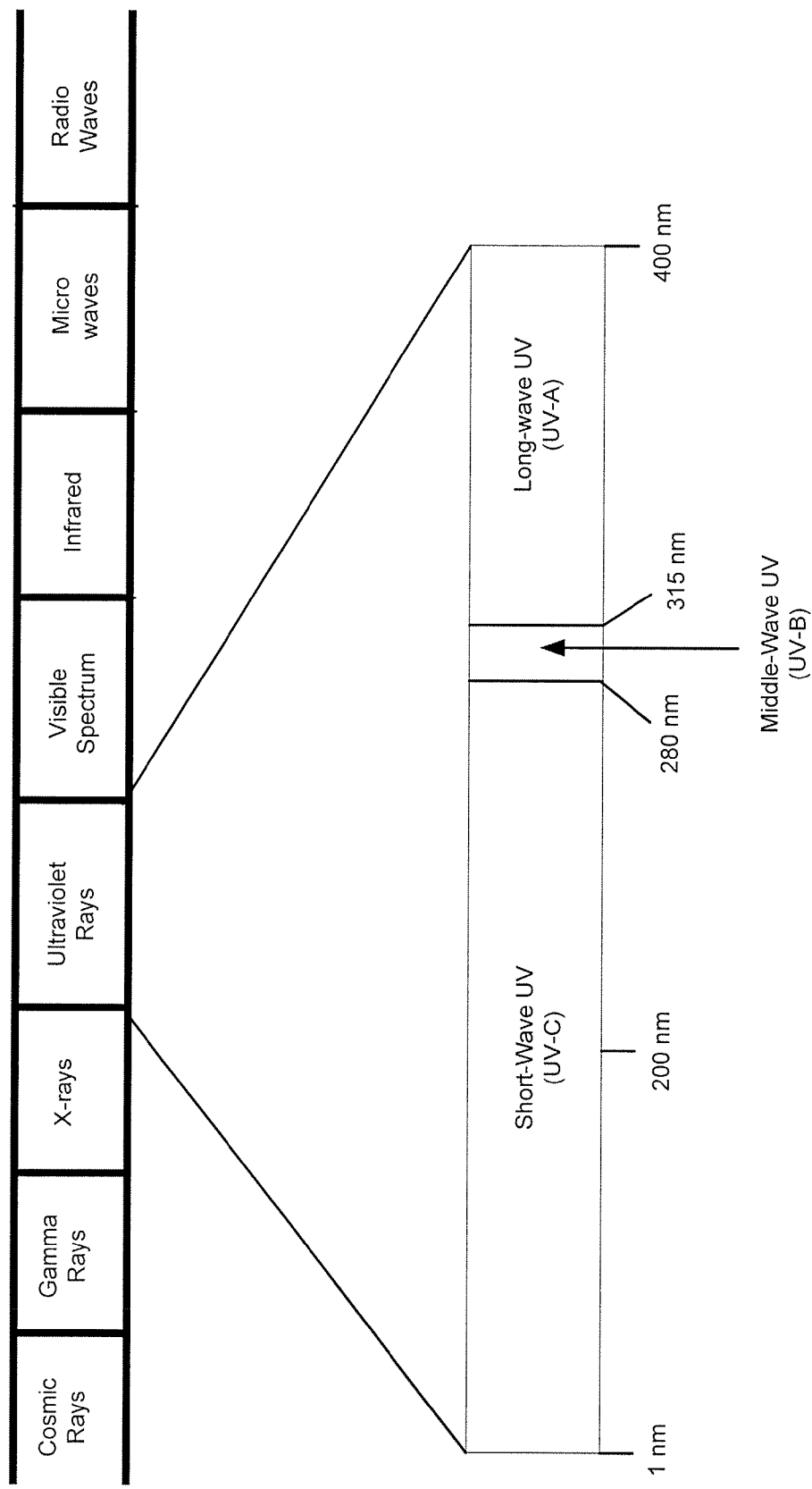
FIG. 1 is a schematic of a range of wavelengths.

FIG. 1 illustrates a spectrum of waves, starting with the smallest on the left and increasing in size towards the right. An expanded portion illustrate ultraviolet (UV) light in is also provided, with UV-A light extending between 400 and 315 nanometers, UV-B light extending between 315 and 280 nanometers and UV-C light being less than 280 nanometers. As a rule, the smaller the wavelength the more power the wave has. Thus, UV-C has a germicidal effect, UV-B is believed to cause cancer and UV-A is believed to cause visual signs of aging. While the sun emits wavelengths across the UV spectrum, the atmosphere substantially blocks wavelengths below about 300 nanometers, thus vast majority of UV light that people are exposed to is UV-A light.

UV-C light is germicidal because it affects the DNA of cells. As is known, DNA consists of the molecules adenine, cytosine, guanine and thymine and the combination of these molecules provide the genetic information for a cell's offspring. Exposing cells to UV-C light causes adjacent thymine molecules in the cell to join. The joining of the adjacent thymine molecules changes the DNA of the cell and prevents the cell from replicating and therefore makes it harmless. While all UV-C light tends to have a germicidal effect, DNA absorption peaks at about 265 nanometers and at about 185 nanometers (thus UV light at or near these wavelengths is more effective as a sterilizing agent). Thus, commercially available standard low pressure mercury-vapor lamps that emit UV light at about 254 nanometers are suitable for use in sterilizing surfaces.

Because of UV-C light's germicidal effects, health agencies that work with infectious diseases have used UV-C light to disinfect surfaces. However, care must be taken as exposure to UV-C is undesirable for individuals.

Turning to FIGS. 2-13, embodiments are disclosed for using UV-C light in a manner that is relatively simple from the user's standpoint while still protecting the user from exposure to UV-C light. A chamber 100 is provided that may enclose an input device such as a keyboard 180 and one or more UV lights 40 may be placed inside the chamber 100. When actuated, the UV lights emit UV-C light and sterilize the keyboard 180. It should be noted that other input devices such as a mouse or touch pad or a lap-top or Tablet PC may be placed in the chamber 100, thus the depicted keyboard 180 is merely an exemplary embodiment.

Figure 2:
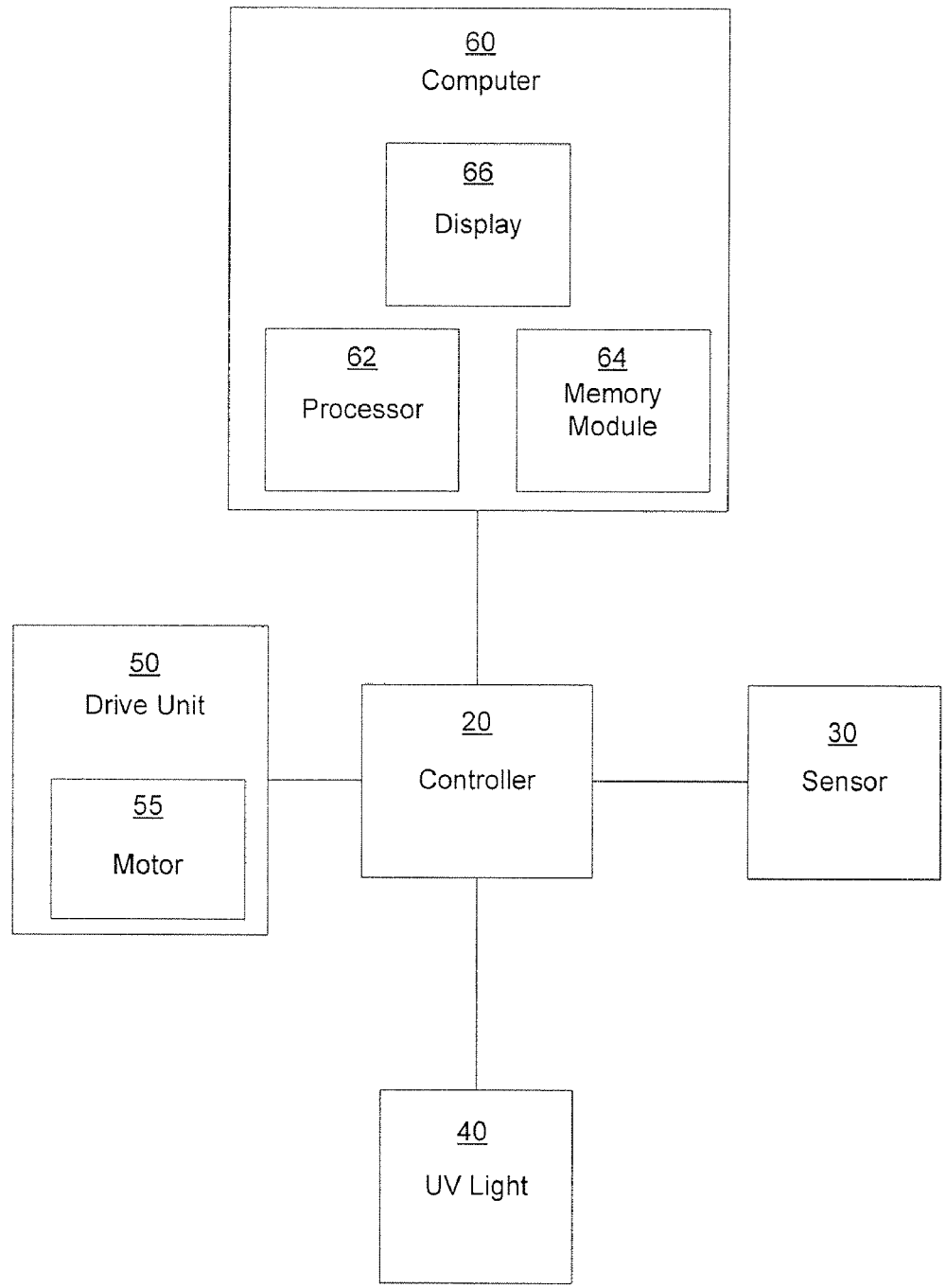
FIG. 2 is a schematic of an embodiment of a control system.

FIG. 2 depicts a system level schematic of embodiments depicted in FIGS. 3-13. A controller 20 is configured to actuate a UV light 40 when a signal is received from a sensor 30. The sensor 30 is configured to provide the signal when the chamber is closed and the UV-C light may be safely applied. A drive unit 50 may be coupled to the controller 20 and may include a motor 55 that is responsive to an actuation from the controller 20. In operation, the motor 55 may open and/or close a door 130 so as to switch the chamber 100 between an open and closed state. The process of closing the door 130 may actuate the sensor 30. The controller 20 may in turn be actuated in response to a trigger. In an embodiment, the trigger may be provided by a computer 60 that includes a processor 62 (which may be a set of processors), a memory module 64 (which may be any desirable medium and may be located locally, remotely or some combination thereof), a display 66 and other components typically included in a computer.

In an embodiment, the computer 60 may include software stored in the memory module that provides the trigger in response to actions taken by a user. For example, when a user state changes (e.g., a user logs out, a user logs in, a user fails to take any action for a period of time, etc. . . . ) the computer 60 may provide a trigger to the controller indicating that a sterilization cycle should begin. Thus, a period of inactivity may automatically cause the computer to trigger the controller 20 to initiate the sterilization cycle. The controller 20 may then provide an actuation input to the drive unit 50 so as to cause the door to close and once a signal is received from the sensor 30 indicating the chamber 100 is closed, the controller 20 may actuate the UV light 40. It should be noted that any type of UV light may be used, thus traditional lamps as well as appropriate light emitting diodes are contemplated as being used for the UV light.

FIGS. 3-9 illustrate embodiments of a system that uses a chamber 100 in a cabinet 200 to sterilize an input device such as a keyboard 180. One advantage of such a system is that it can accept a wide variety of input devices and therefore is can be readily used, for example, with existing keyboards. Furthermore, the chamber may also be used to sterilize associated input devices such as a computer mouse simultaneously with a keyboard.

The chamber 100 may include one or more UV lights 40. In an embodiment, the chamber may include reflective surfaces that help redistribute light emitted from the one or more UV lights 40 as illustrated. If provided, some or all of the reflective surfaces may also be shaped to help direct the emitted light in a more desirable pattern. A drawer 150 is mounted in a track 120 and is configured to support a keyboard 180 and/or other input devices and may also include reflective materials. A door 130 is provided on the chamber 100 so that the chamber 100 may be switched between an open and closed state. The door 130 may be located by a door positioner 135 that may be a simple hinge. In an alternative embodiment, the door positioner 135 may be configured to bias the door 130 toward an open position and the door positioner 135 may be controlled by a motor or by a linkage. For example, the door positioner 135 may include a biased hinge 136 and a linkage 137 that is actuated by the drawer 150. Thus, the hinge 136 may be configured to bias the door 130 toward an open position (by, for example, the use of a coil spring) while the linkage 137 is configured to translate the door 130 toward a closed position when the drawer 150 pushes against the linkage 137. Thus, the movement of the drawer 150 can be configured to automatically close the chamber 100. As can be appreciated, numerous other methods of controlling the position of the door 130 are possible, such as using motors, springs and the like.

The drawer 150 may be mounted on a track 120 that may include a groove 121 and track elements 122 that fit into or ride along the groove 121. In operation, the track 120 controls the translation of the drawer 150. In an embodiment, the translation may be along a linear path and the track 120 may allow the drawer 150 to be substantially translated from within the chamber 100 to mostly out of the chamber 100.

Figure 3:
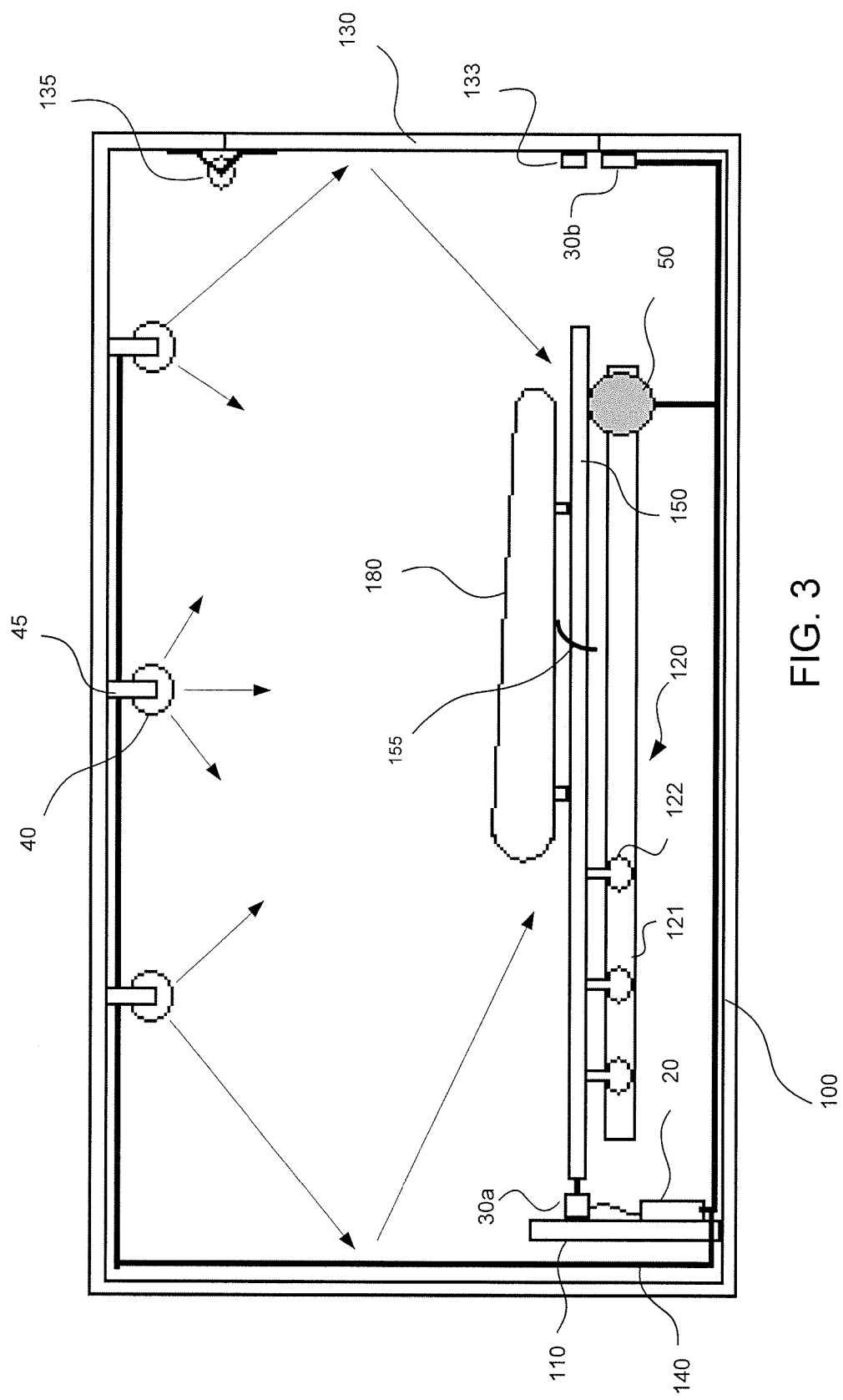
FIG. 3 is a schematic of an embodiment of a chamber that may be used to sterilize an input device.
Figure 4:
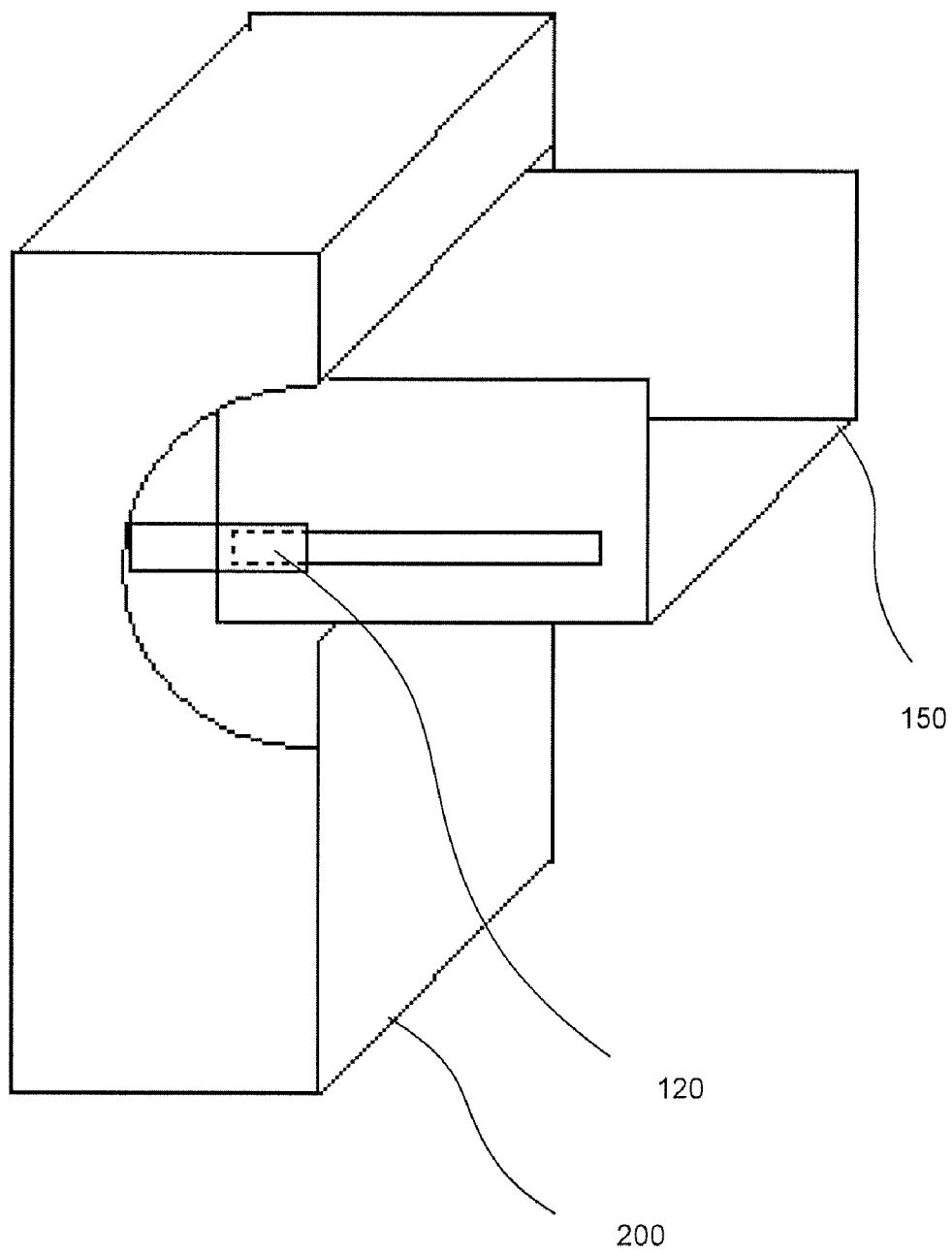
FIG. 4 is an isometric view of an embodiment of a cabinet with a portion cutaway to illustrate an embodiment of a drawer track.

As depicted in FIG. 3, the translation of the drawer 150 may cause a sensor 30a to be actuated. The sensor 30a is representative of a contact sensor that is actuated by displacement; however, any other desirable sensor technology may be used. For example, but without limitation, a sensor 30b may be configured to detect when the door 130 is closed by detecting a door element 133, which may be a magnet, being brought into proximity to the sensor 30b. In an alternative embodiment, sensor 30a and/or sensor 30b may be an optical sensor. To receive the signal from the sensor, the controller 20 is in communication with the sensor 30 via the communication path 140 and the communication path 140 also extends to the UV light 40 (three of which are shown in FIG. 3). It should be noted that the communication path 140 may also be configured to transmit both signals and power over the same wires. However, the communication path 140 may be include a number of separate wires and therefore is shown as a single element for purposes of clarity. It should be noted that sensor 30 may be positioned in other locations as desired, depending on the type of sensor used as well as the configuration of the chamber 100.

To position the sensor 30a and controller 20, a support 110 may be provided. It should be noted that multiple supports 110 may be provided as desired, but only one is shown for the sake of clarity. As can be appreciated, additional supports 110 may also be used to support additional and/or other elements.

While three UV lights 40 are shown in FIG. 3, in an embodiment one UV light may be used. In an alternative embodiment, more than three UV lights 40 may be used. If additional UV lights are used, the system can provide the advantage of providing a greater range of angles of UV light being directed onto an input device and may also help reduce the time required to sterilize the input device. In an embodiment where the input device is a keyboard, the keyboard 180 can be made of a material that is UV light translucent so as to maximize exposure of surfaces of the keyboard 180 to the UV light. To facilitate light distribution, one or more reflectors may be positioned in the chamber so as to direct UV light onto the keyboard 180 from different angles. If desired, an inner surface 105 of the chamber 100 may be made of a UV reflective material so as to further facilitate distribution of the UV light. In addition, the drawer 100 may also be made of a UV reflective material so as to further facilitate UV light distribution.

Figure 5:
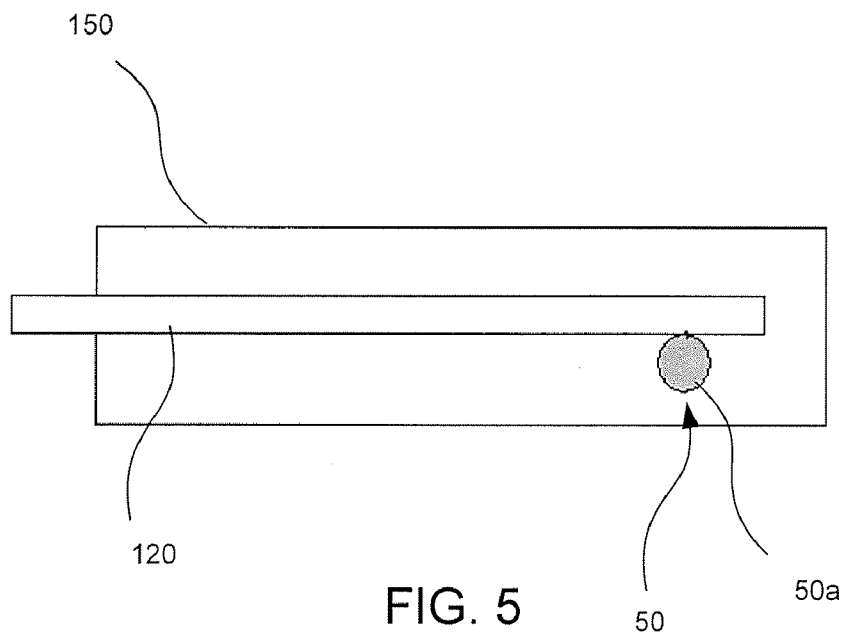
FIGS. 5 and 6 are schematic views of embodiments of drive unit configurations.
Figure 6:
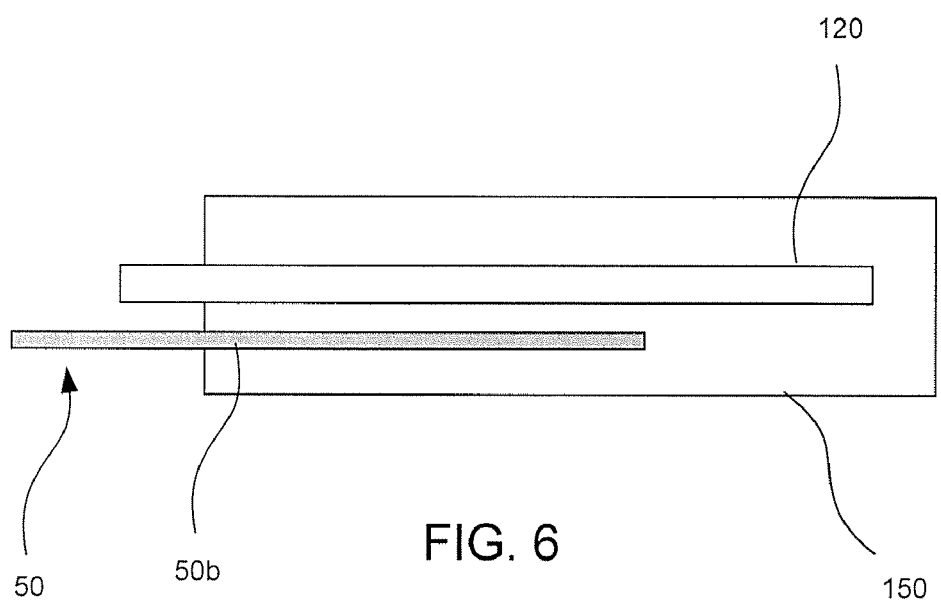

FIGS. 5 and 6 illustrate two embodiments of possible drive units 50. In an embodiment as depicted in FIG. 6, the drive unit 50a may be configured to rotate so as to cause the drawer 150 to translate. As can be appreciated, such an embodiment may be powered by any drive unit 50 configured to convert potential energy to mechanical energy, such as but without limitation, a spiral spring. Thus, the movement of the drawer 150 between a sterilize position where the drawer 150 is positioned in the chamber 100 (and where the keyboard 180 may be sterilized) and an operative position where the drawer 150 extend outside the chamber 100 (and where the keyboard 180 may be typed on) may cause the drive unit 50a to store potential energy. For example, the movement could cause the drive unit 50a to wind up a spiral spring element. Once an activation input was provided to the drive unit 50, the stored potential energy would be converted to mechanical energy and could cause the drawer 150 to translate back to the prior position (e.g., from the operative position to the sterilization position). The drive unit 50a may also comprise a motor 55 configured to interact with the drawer 150 or the track 120 though, for example, a gear and pinion system or a pulley system so as to causes the drawer 150 to translate between the operative position and the sterilize position in response to a signal received from the controller 20.

In another embodiment, such as depicted in FIG. 6, the drive unit 50b may be configured to provide a linear force to translate the drawer 150. In an embodiment, the drive unit 50*b* could be a coiled spring. In another embodiment, the drive unit 50*b* could be a worm drive driven by a motor 55. In an alternative embodiment, the drive unit 50*b* may be a piston. However, any other desirable configuration of the drive unit 50*b* may be used. It should be noted that if the drive unit 50 includes a motor 55, the system may be configured to provide for a completely automated sterilizing cycle.

Figure 7:
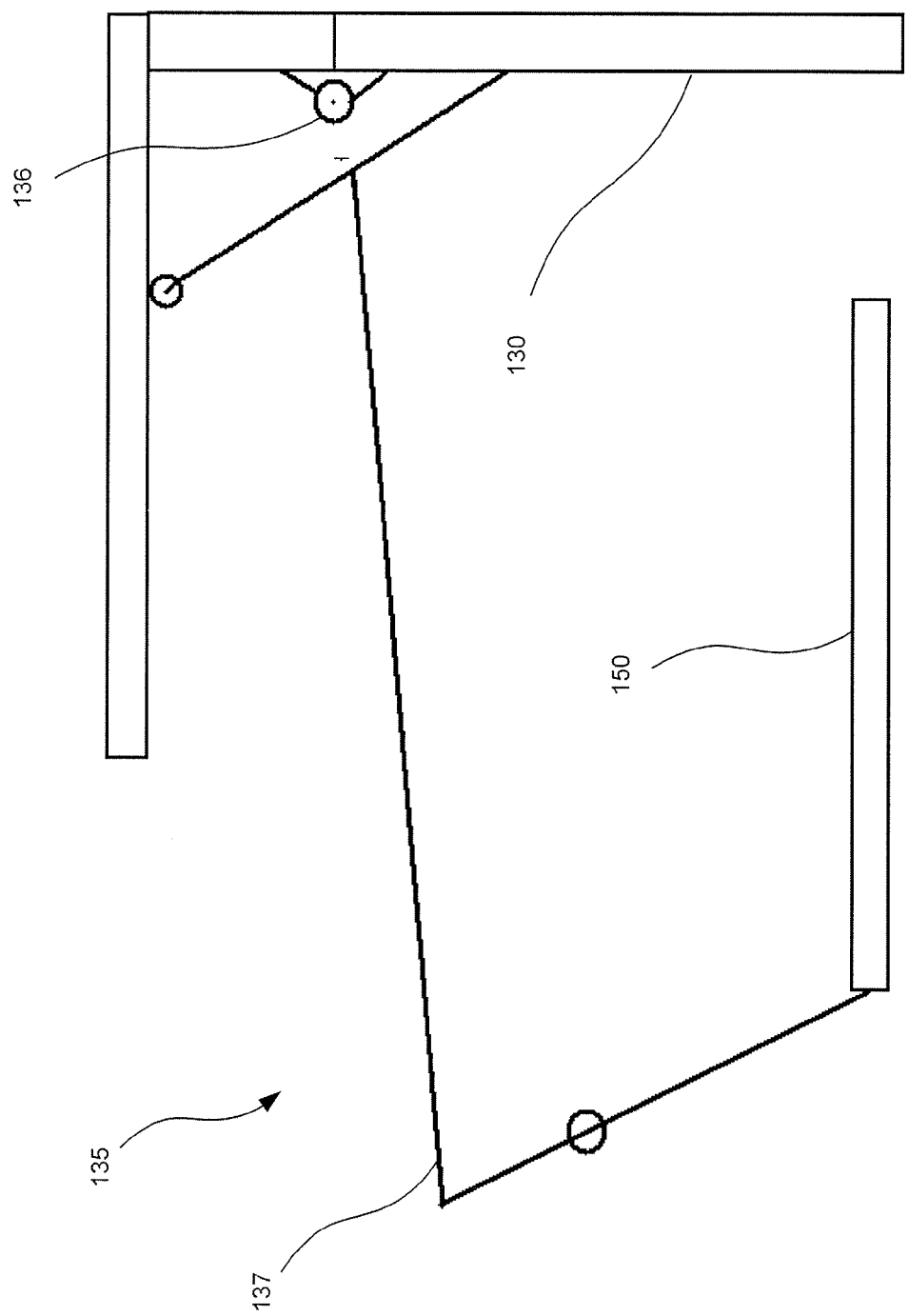
FIG. 7 is a schematic view of an embodiment of a door positioner.
Figure 10:
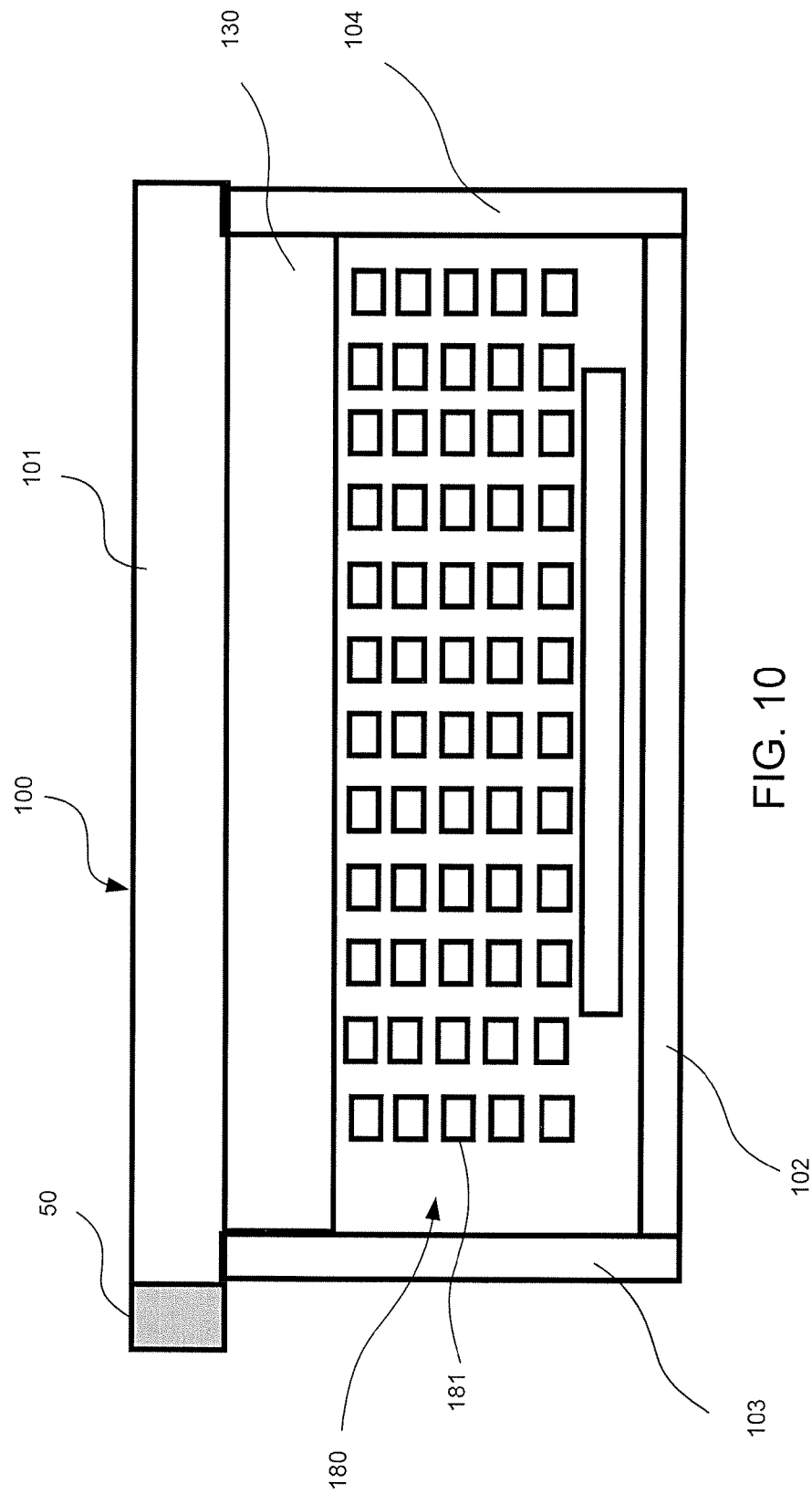
FIG. 10 is a schematic top view of an alternative embodiment of a chamber.
Figure 11:
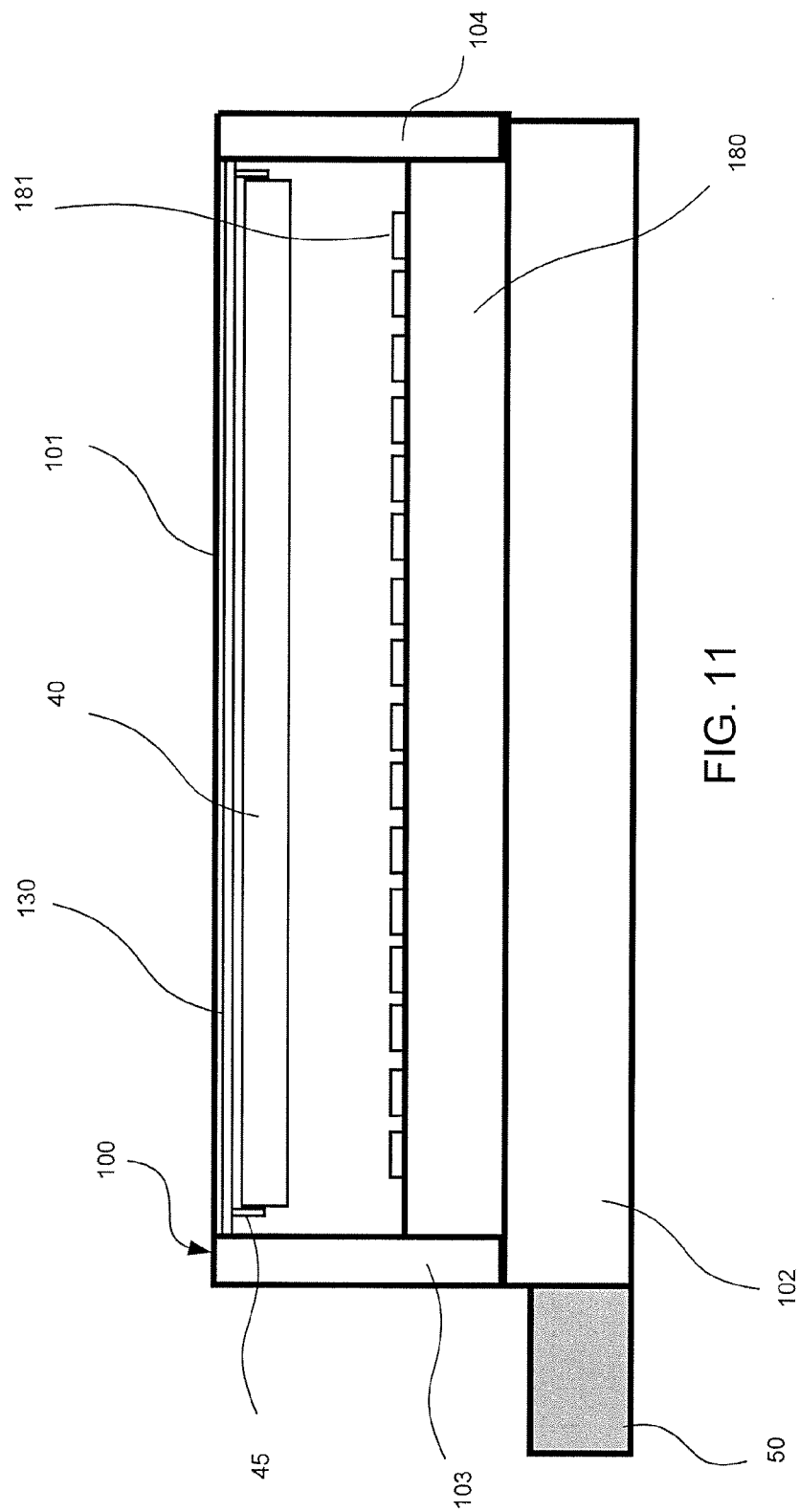
FIG. 11 is a schematic front view of the embodiment depicted in FIG. 10

As noted above, to ensure UV-C light is kept entirely or substantially within the chamber 100, a sensor 30 may be provided to detect when the chamber 100 is closed. While the sensor 30 may be configured to directly sense the closing of a door 130, in an alternative embodiment the door positioner 135 may include a biased hinge 136 and a linkage 137 such as is depicted in FIG. 7. In such an embodiment, translation of the drawer 150 into the chamber 100 presses against the linkage 137 and the links transmits a force to the door 130 that causes it to close (overcoming the force exerted by the biasing hinge 136 in the process). Once the drawer 150 is moved away from the sterilize position, the biasing hinge 136 will urge the door 130 toward an open position. Thus, an advantage of such an embodiment is that the sensor 30 can be configured to detect the drawer 150 being in the sterilize position because the door 130 will be closed if the drawer 150 is in the sterilize position.

In an alternative embodiment, as depicted in FIGS. 8 and 9, the door 130 may be mounted to a drawer 150 that is mounted to a cabinet 200 via a track 120 and translation of the drawer 150 can cause a first feature 132 to press against a cabinet surface 201. This can the door 130 to rotate about the door positioner 135 so that the door 130 is sealed to the cabinet 200 by a door seal 131 and the first feature 132. Thus, numerous methods of closing the chamber 100 are possible.

As noted above, a trigger may be provided by a computer in response a change in states. In an alternative embodiment, the trigger may be provided by a user pressing a lever 155 (or some other similar mechanical device). In an embodiment, the lever 155 may engage a feature (not shown) of the chamber 100 and hold the drawer 150 in the operative position by resisting the force being exerted on the drawer 150 by the drive unit 50. Once actuated, the lever 155 will cease to engage the feature and the drive unit 50 will cause the drawer 150 to move toward to the sterilize position. If the door 130 is configured so that the translation of the drawer 150 causes the door 130 to close, the trigger provided by pressing the lever 155 can effectively be the trigger that causes the UV light to be activated.

In an alternative embodiment, the drawer 150 may require the user to exert a force to be moved to the sterilizing position and once the sterilizing cycle is complete, the drawer 150 may urged into the operative position by the drive unit 50 automatically.

FIGS. 10-13 illustrate an alternative method of closing a chamber 100 by integrating the chamber 100 into the keyboard 180. A keyboard 180 includes keys 181 and is positioned between a first side 101, a second side 102, a third side 103 and a fourth side 104 of the chamber 100. A drive unit 50 is provided to cause a door 130 to be moved along a track 120. This may position one or more UV lights 40 over the keyboard keys 181. The door 130 may be flexible and travel along a groove 121 and may also be directed over one or more rollers 123, which may be positioned by supports 124. In an embodiment, a roller 123 may be combined with the drive unit 50.

In operation, the drive unit 50 can cause the door 130 to translate from an open position to a closed position so as to cause the chamber 100 to switch between an open state and a closed state. In an embodiment, a sensor 30 may be provided to detect when the door 130 is in the closed position and it is safe to actuate the UV lights.

Figure 12:
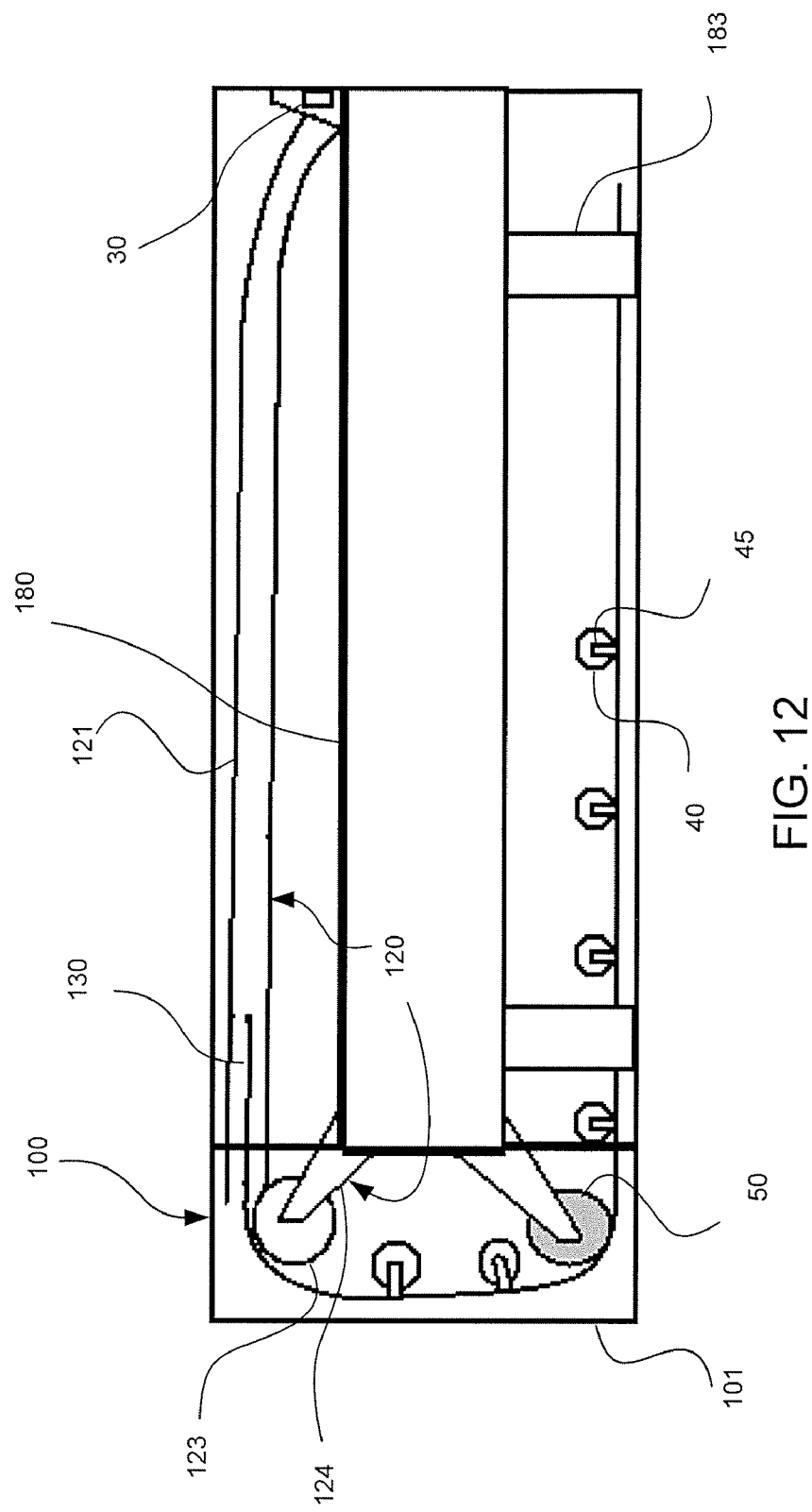
FIG. 12 is a schematic cross-section of the embodiment depicted in FIG. 10 with the chamber in an open state.
Figure 13:
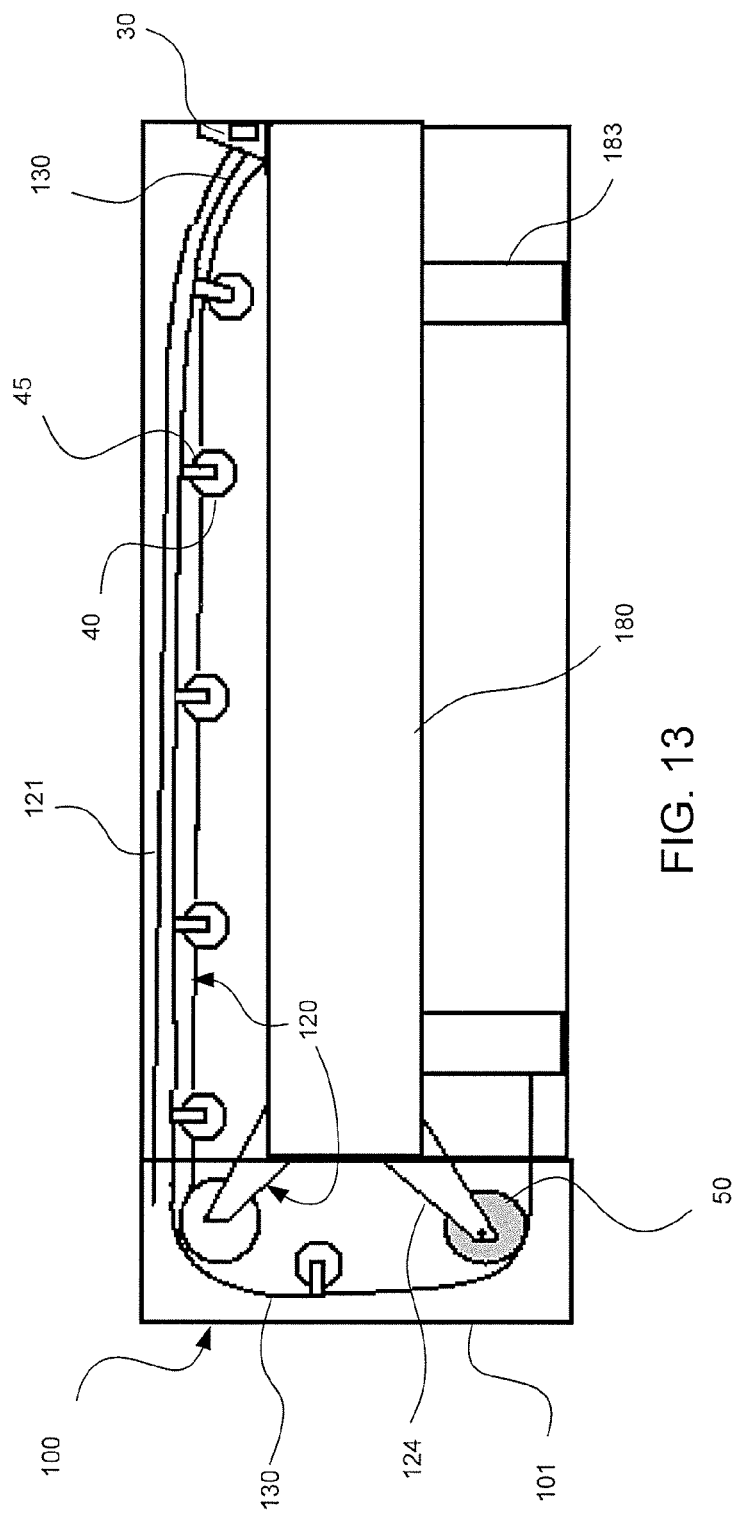
FIG. 13 is a schematic cross-section of the embodiment depicted in FIG. 10 with the chamber in a closed state.

In an embodiment, the UV lights 40 may be mounted to the door 130 so that when the door 130 is in the closed position, the UV lights 40 are brought into position from under the keyboard 180 so that they may effective sterilize the keys of the keyboard 180, as depicted in FIGS. 12 and 13. As can be appreciated, a flexible power delivery system is required to allow the power to be delivered to the UV lights 40 when they are brought into position. In an embodiment, this may be accomplished by providing a retractable insulated wire (not shown) that is coupled to a set of conductors built into the door. In an alternative embodiment, a set of contacts can be provided on the door 130 and another set of contacts can be provided on the chamber 100 or the track 120. In such an embodiment, the contacts on the door 130 may be configured to engage the contacts provided on the chamber 100 or track 120. Thus, a voltage applied to the contacts provided to the chamber 100 or track 120 will also apply a voltage across the contacts on the door 130 so that power may be provided to the lights mounted to the door 130. To provide sufficient space under the keyboard 180, the keyboard 180 may be mounted on supports 183. In an embodiment, the keyboard keys 181 may be made of UV-C translucent materials so as to facilitate sterilization of the keyboard 180. As can be appreciated, an advantage of this configuration is that the keyboard 180 and the chamber 100 may be made smaller and the cabinet is not required.

In an alternative embodiment, the UV lights 40 may be positioned within the keyboard 180 and the keyboard 180 and the keys 181 may be made of UV-C translucent materials so that the UV lights 40 may sterilize the keyboard 180 from within. In such an embodiment, the door 130 may omit the UV lights 40 and simply be used to switch the chamber 100 between open and closed states. One advantage of such a configuration is that there is no need to provide flexible wires for power delivery or to otherwise configure the door 130 to provide electricity to the UV lights 40. As discussed above, to prevent untimely actuation of the UV lights 40, the sensor 30 may be used to prevent operation of the UV lights 40 until the chamber 100 is in the closed state.

As noted above, the use of a motor is beneficial because it allows the sterilization system to functional automatically. As can be appreciated, if the sterilization cycle happens automatically, there is no need to rely on users and the element of user error is removed so that the sterilization may occur with greater reliability.

In an embodiment, a change in the user state (such as the user logging off, or a timeout occurring) in a computer associated with the keyboard will cause software to trigger the controller 20 to actuate the motor 165 in the drive unit 50 so as to cause the chamber to be switch to a closed state. Once the controller 20 receives a signal from the sensor 30 that the chamber is in a closed state, the controller will actuate the UV lights 40 and sterilize the keyboard 180. Once the sterilized cycle completes, the controller 20 may shut off the UV lights 40 and switch the chamber 100 back into the open or operative state, in the process placing the door 130 in the operative position. This may be accomplished by providing a second signal to the drive unit 50 from the controller 20 so as to cause the drive unit 50 to switch the chamber 100 back to the open state. Thus, in an embodiment, the sterilization process may take place in an automated manner without the need for user intervention.

It should be noted that automated sterilization prevents the problems associated with manual actuation of the sterilization procedure. For example, in a high stress situation an individual might forget to properly sterilize the input device. However, if the sterilization takes place automatically, then human error will not be a factor in whether an input device is sterilized. This also minimizes the need to train individuals in the proper sterilizing procedures and can reduce the cost of hiring new personal.

In an embodiment, a status signal may be provided by the controller 20 so as to indicate the progress of the sterilization cycle. If a computer is configured to process the status signal, a visual depiction of the status can be provided on a display. The advantage of such a configuration is that a potential user can quickly determine the time remaining before the sterilization cycle is complete and therefore can utilize his or her time more efficiently.

It should also be noted that the trigger may be provided in a wireless manner. In such a configuration the controller may be equipped for wireless communication with the computer and/or the input device and a signal from the computer or the input device may trigger the sterilization cycle. In an embodiment, the controller may be configured to provide a sterilization complete signal once the sterilization cycle is complete. While not required, the sterilization complete signal allows a software application to switch between states and may allow a computer to prompt a user to take an action such as open the drawer or to log in. In an embodiment, a computer may be configured to provide a trigger initiating the sterilization signal in response to a lack of user input or a change in user states such as the user logging out. Upon receipt of the sterilization signal, the computer may delay providing another request for sterilization until the input device is used.

As can be appreciated, the described system will require a power source to actuate the lights (and power the motor, if provided). Any desirable power source may be used, including but not limited to a battery, an ultra capacitor, and A/C power (which may be converted to DC power using a power supply in a known manner).

As can be appreciated, the time for effective sterilization may vary depending on the number of UV lights and the output thereof. However, it is expected that a standard sterilization cycle will be sufficient for most input devices. Therefore, in an embodiment the sterilization cycle may be for a predetermined period of time. In an alternative embodiment, the sterilization cycle may be programmable.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Numerous other embodiments, modifications and variations within the scope and spirit of the appended claims will occur to persons of ordinary skill in the art from a review of this disclosure.

What is claimed is:

1. A system for disinfecting a surface of an input device, comprising:
    a chamber configured to enclose the surface of the input device, the chamber switchable between an open state and a closed state, the chamber including a drawer configured to support the input device, the drawer moveable between an operative position and a sterilize position;
    a door configured to be automatically closed when the drawer is in the sterilize position;
    a sensor configured to provide a signal when the chamber is in the closed state;
    a plurality of UV lights that are mounted to the door, so that when the door is in a closed position, the plurality of UV lights are positioned under the input device so that each of the plurality of UV lights is entirely below the input device; and
    a controller configured to cause the drive unit to switch the chamber to the closed state in response to a trigger requesting activation of the UV light and to activate the UV light in response to the signal received from the sensor.

2. The system of claim 1, wherein the drive unit is configured to automatically translate the drawer between the operative position and the sterilize position in response to an actuation input received from the controller.

3. The system of claim 2, wherein the drive unit comprises a motor and the controller is configured to actuate the motor of the drive unit in response to the trigger.

4. The system of claim 1, wherein the controller is configured to provide a signal indicating a status of a sterilization cycle.

5. The system of claim 1, wherein the controller is configured to receive the trigger from a computer coupled to the input device.

6. A method of sterilizing a surface of an input device in a chamber, comprising:
    (a) receiving a trigger in response to a detection of a period of user inactivity, the trigger requesting a sterilization cycle to begin;
    (b) providing an actuation input to a drive unit in response to the trigger, the drive unit configured to switch the chamber between an open and a closed state by positioning a drawer that supports the input device, the drawer being positioned between an operative position and a sterilize position, the operative position corresponding to the open state of the chamber and the sterilize position corresponding to the closed state of the chamber;
    (c) determining that the chamber is in a closed state; and
    (d) actuating a UV light for a predetermined time, the UV light comprising UV-C light having a wavelength of less than 280 nanometers, UV lights being directed onto the input device by one or more reflectors in the chamber and by UV reflective material on one or more inner surfaces of the chamber.

7. The method of claim 6, wherein the receiving the trigger in (a) comprises:
    (i) providing a signal to a motor; and
    (ii) switching the chamber from the open state to the closed state with the motor.

8. The method of claim 6, wherein the drive unit comprises a motor and the providing of the actuation input in (b) comprises:
    (i) providing a signal to the motor; and
    (ii) switching the chamber from the open state to the closed state with the motor.

9. The method of claim 6, wherein the determining in (c) comprises:
    (i) receiving a signal from a sensor indicating that the chamber is in a closed state.

10. The method of claim 6, further comprising:
    (e) in response to the actuating in (d), switching the chamber to an open state.

11. The method of claim 6, further comprising:
    (e) providing a sterilization complete signal.

12. The method of claim 6, wherein a controller in the chamber is configured to receive a wireless signal, the method further comprising:
   (i) receiving the wireless signal from the input device, the wireless signal triggering the sterilization cycle to begin.

13. A system for sterilizing a surface of an input device, comprising: a chamber configured to switch between an operative state and a closed state;
   a computer including software that detects a period of user inactivity and that initiates a sterilization cycle when the period of user inactivity is detected;
   a keyboard having a housing coupled to the chamber, the chamber including a drawer configured to support the input device, the drawer being moveable between a first position wherein the keyboard is at least partially exposed outside of the chamber, and a second position wherein the keyboard is contained within the chamber, and the keyboard including an operative surface;
   a UV light configured to sterilize the operative surface when the chamber is in the closed state, the UV light comprising UV-C light having a wavelength of less than 280 nanometers;
   one or more reflectors positioned in the chamber to direct the UV light onto the keyboard;
   a sensor configured to provide a signal when the chamber is in the closed state; and
   a controller configured to actuate the UV light in response to the signal provided by the sensor.

14. The system of claim 13, wherein the chamber includes a flexible door positioned in a track, wherein the flexible door is configured to be translated between an operative position and a sterilize position, wherein translating the flexible door to the sterilized position switches the chamber to the closed state.

15. The system of claim 14, wherein the keyboard further includes a drive unit configured to automatically translate the flexible door between the operative and the sterilize position in response to an actuation input.

16. The system of claim 15, wherein the drive unit comprises a motor coupled to the flexible door, the motor configured to translate the flexible door between the operative and the sterilize position.

17. The system of claim 15, wherein the controller is configured to actuate the UV light in response to a trigger and the controller is further to provide the actuation input to the drive unit in response to the trigger.

18. The system of claim 13, wherein the keyboard is fixably attached to the chamber.

19. The system of claim 13, wherein the chamber includes a door, wherein the door is configured to be translated between an operative position and a sterilize position, wherein translating the door to the sterilized position switches the chamber to the closed state.

* * * * *